United States Patent [19]

Ashworth

[11] Patent Number: 4,922,763
[45] Date of Patent: May 8, 1990

[54] METHOD AND AN APPARATUS FOR TAKING SOIL SAMPLES

[76] Inventor: John Ashworth, 9938 - 67 Avenue, Edmonton, Alberta, Canada, T6E 0P5

[21] Appl. No.: 224,567

[22] Filed: Jul. 26, 1988

[51] Int. Cl.⁵ .............. G01N 1/04; G01N 1/08
[52] U.S. Cl. .................. 73/864.41; 83/919; 175/58
[58] Field of Search ............ 73/864.41, 864.51; 83/919; 175/58

[56] References Cited

U.S. PATENT DOCUMENTS

| | | | |
|---|---|---|---|
| 2,689,718 | 9/1954 | Headlee et al. | 73/864.41 X |
| 3,625,296 | 12/1971 | Mabry et al. | 73/864.41 X |
| 4,304,139 | 12/1981 | Johnson | 73/864.32 |
| 4,356,734 | 11/1982 | Ivancsics | 73/864.41 X |
| 4,442,721 | 4/1984 | Singer | 73/863.31 |
| 4,828,047 | 5/1989 | Rogerson | 175/58 X |

FOREIGN PATENT DOCUMENTS

| | | | |
|---|---|---|---|
| 440466 | 4/1947 | Canada . | |
| 526426 | 6/1956 | Canada . | |
| 533358 | 11/1956 | Canada . | |
| 566349 | 11/1958 | Canada . | |
| 574117 | 4/1959 | Canada . | |
| 639198 | 4/1962 | Canada . | |
| 683117 | 3/1964 | Canada . | |
| 728375 | 2/1966 | Canada . | |
| 765166 | 8/1967 | Canada . | |
| 901024 | 5/1972 | Canada . | |
| 1154466 | 9/1983 | Canada . | |
| 1186703 | 5/1985 | Canada . | |
| 238867 | 3/1969 | U.S.S.R. | 73/864.41 |
| 626381 | 8/1978 | U.S.S.R. | 73/864.41 |
| 669252 | 6/1979 | U.S.S.R. | 73/864.41 |
| 718752 | 2/1980 | U.S.S.R. | 73/864.41 |
| 763721 | 9/1980 | U.S.S.R. | 73/864.41 |
| 1060973A | 12/1983 | U.S.S.R. . | |
| 533490 | 2/1941 | United Kingdom | 73/864.41 |

*Primary Examiner*—Tom Noland
*Attorney, Agent, or Firm*—Davis, Bujold & Streck

[57] ABSTRACT

A method of taking soil samples consisting of the steps of; cutting at least one slit trench along a path transverse to bands of fertilizer in the soil; and taking a thoroughly intermixed sample from the cuttings. The samples are taken using a chain saw with a soil sampling attachment. The soil sampling attachment consists of a container with an open mouth having a slot across the mouth. A blade of a chain saw is disposed in the slot. Upon activation of the chain saw soil cuttings drop from the blade through the mouth to accumulate in the container. A bracket secures the container to the chain saw.

6 Claims, 4 Drawing Sheets

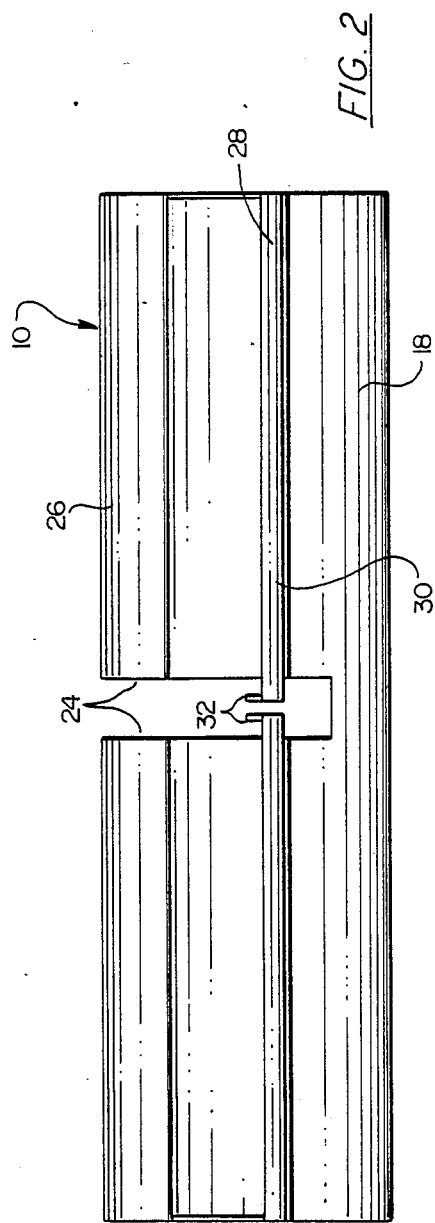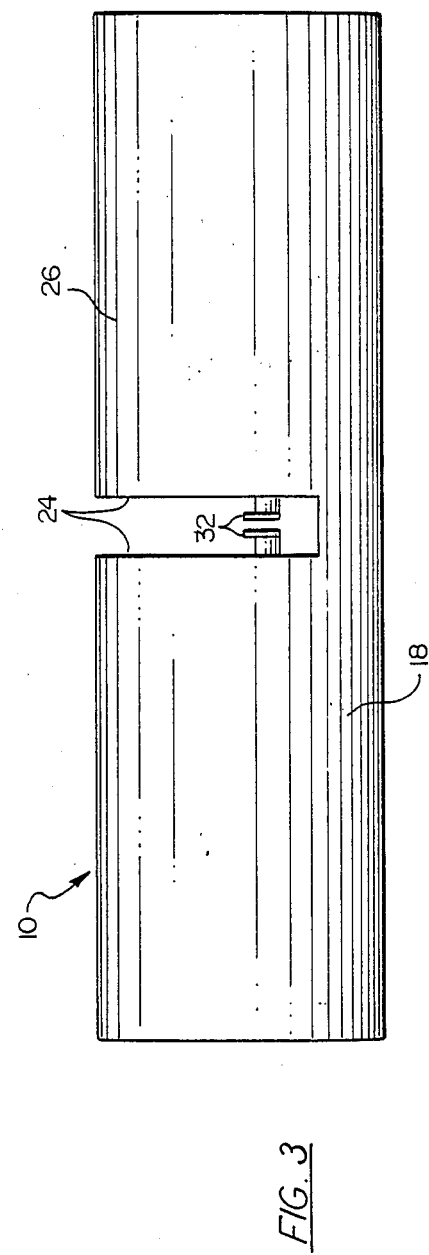

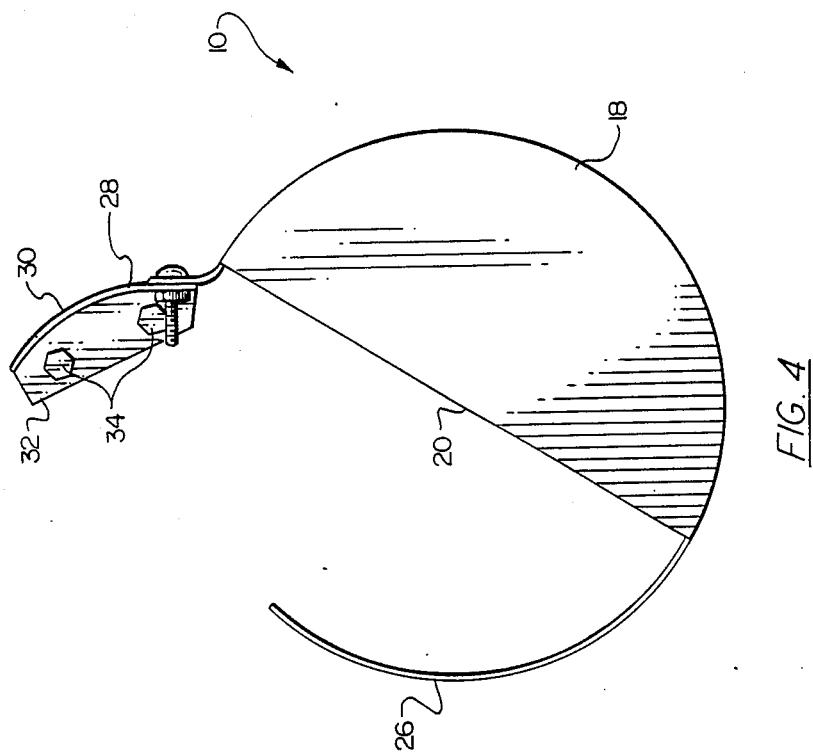

METHOD AND AN APPARATUS FOR TAKING SOIL SAMPLES

The present invention relates to a method and an apparatus for taking soil samples.

BACKGROUND OF THE INVENTION

Most fertilizer is now applied to farmlands in bands. These bands vary in spacing between 7 and 16 inches. An agronomist will always take soil samples to determine the extent of residual fertilizer in the soil prior to making recommendations on fertilizer application. The soil samples are taken using a coring method at a plurality of points on the farmland. It is recognized that the existence of banding will tend to distort the validity of the samples obtained. If few samples are taken there is a possibility that the majority of the samples will be either on or between the fertilizer residue bands. It is for this reason that multiple samples are taken. It is recommended that the samples number a minimum of 12 and preferably 20 or more; however time constraints often dictate that the agronomist take less than the optimum number of samples.

SUMMARY OF THE INVENTION

What is required is a method and apparatus for taking soil samples which will not be as prone to distortion caused by fertilizer banding.

According to one aspect of the invention there is provided a method of taking soil samples which is comprised of the steps of cutting a slit trench along a path transverse to bands of fertilizer in the soil; and taking a thoroughly intermixed sample from the cuttings.

Although beneficial results may be obtained by using the method described, it took the Applicant a lot of experimentation to find a tool which could cut a trench suitable for obtaining a soil sample. Accordingly, even more beneficial results may be obtained if the trench is cut using a blade of a chain saw. The blade of the chain saw should be modified to have a plurality of equally spaced tooth-like projections.

Although beneficial results may be obtained by using the method described, a chain saw is difficult to handle unless the correct technique is known. Accordingly, even more beneficial results may be obtained by engaging the blade of the chain saw in the soil and then dragging the chain saw backwards to form a slit trench.

Although beneficial results may be obtained by using the method described, it is difficult to obtain a thoroughly intermixed sample from the cuttings which accumulate at the side of the trench. Even more beneficial results may be obtained by using the apparatus preferred by the Applicant to gather intermixed samples.

Accordingly to this further aspect of the invention there is provided a soil sampling attachment for a chain saw which is comprised of a container with an open mouth having a slot across the mouth. A blade of a chain saw is disposed in the slot. Upon activation of the chain saw soil cuttings drop from the blade through the mouth to accumulate in the container. Means are provided for securing the container to the chain saw.

Although beneficial results may be obtained by using the soil sampling attachment as described, the soil cuttings tend to spray such that the clothing of the operator may become soiled. Even more beneficial results may therefore be obtained with the addition of the preferred feature of a mud guard extending partially over the mouth of the container such that cuttings are confined.

Although beneficial results may be obtained by using the soil sampling attachment as described, it is preferable if there is consistency in the depth of sample taken. Even more beneficial results may therefore be obtained with the addition of the preferred feature of a guide attached to the container such that the upon the guide engaging a groundsurface the chain saw blade is maintained at a preselected depth and angle of penetration.

BRIEF DESCRIPTION OF THE DRAWINGS

These and other features of the invention will become more apparent from the following description in which reference is made to the appended drawings, wherein:

FIG. 2 is a front elevation view of the soil sampling attachment for a chain saw as illustrated in FIG. 1.

FIG. 3 is a rear elevation view of the soil sampling attachment for a chain saw as illustrated in FIG. 1.

FIG. 4 is a side elevation view of the soil sampling attachment for a chain saw as illustrated in FIG. 1.

DETAILED DESCRIPTION OF THE PREFERRED EMBODIMENT

Figure 1:
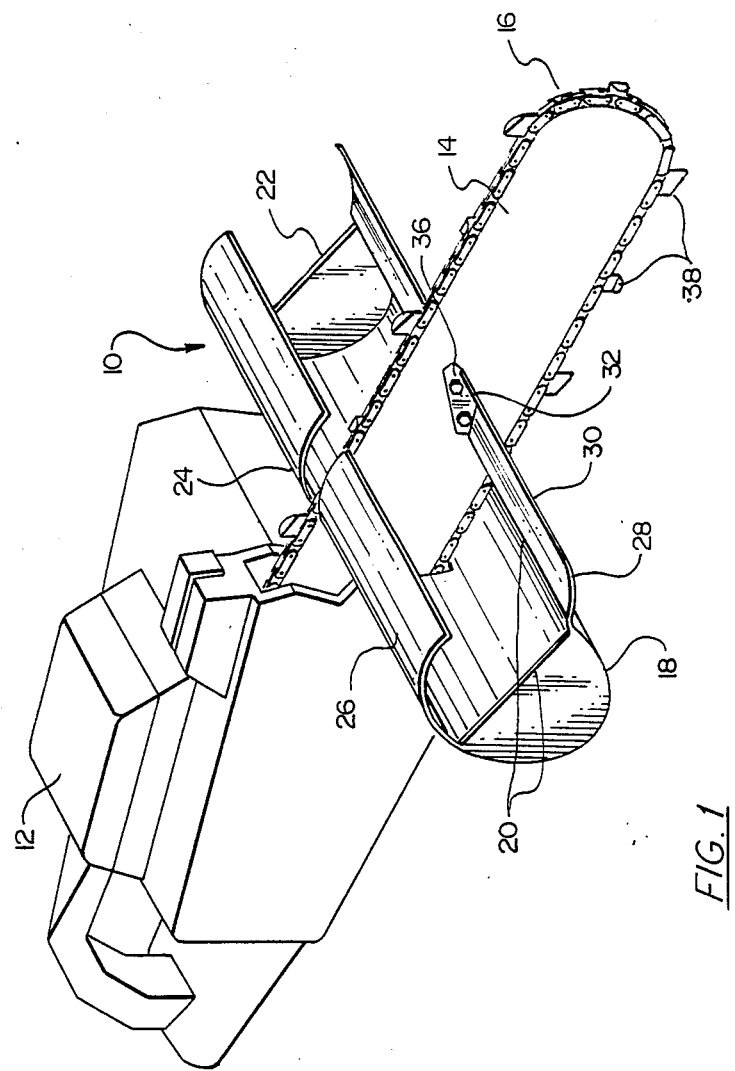
FIG. 1 is a perspective view of a preferred embodiment of the invention.
Figure 6:
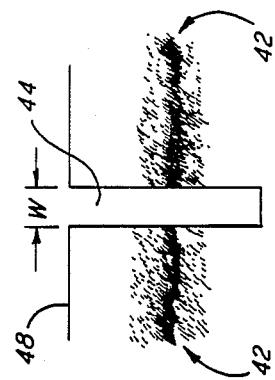
FIG. 6 is a diagrammatic cross-section of the slit trench of FIG. 5.
Figure 5:
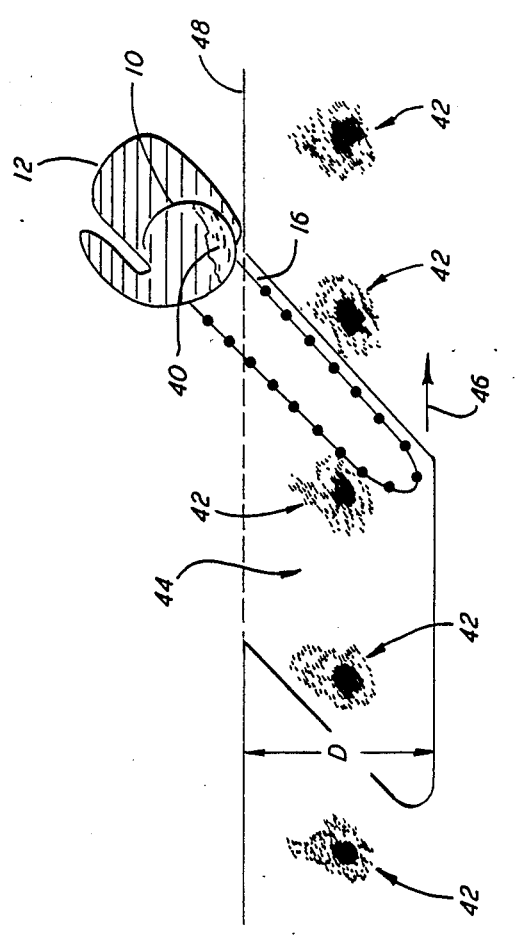
FIG. 5 is a diagrammatic view illustrating in elevation the cutting of a slit trench according to the present invention.

The preferred embodiment will now be described with reference to FIGS. 1 through 4. The preferred embodiment, generally designated by reference numeral 10, is a soil sampling attachment for a chain saw. For the purpose of this description the chain saw will be designated by reference numeral 12 with its primary components of a blade and a continuous chain designated by numerals 14 and 16 respectively.

Soil sampling attachment 10 consists of an elongate container 18 with a peripheral edge 20 defining an open mouth 22. A slot 24 extends transversely across mouth 22. A mud guard 26 is integrally formed as part of container 18. Mud guard 26 extends from peripheral edge 20 partially over mouth 22. A guide 28 in the form of an angled flange is attached peripheral edge 20 of container 18. Guide 28 has a contact surface 30. A bracket 32 is integrally formed as part of guide 28. Bracket 32 has holes 34 through which pass bolts 36.

Soil sampling attachment 10 was especially developed to enable soil samples 40 to be taken in accordance with a new method the results of which are less prone to distortion caused by fertilizer banding. The theory behind the method is that banding distortion can be reduced by taking samples along a path which traverses the bands 42. In its basic form the method consists of the steps of firstly, cutting a slit trench 44 along a path transverse to bands of fertilizer in the soil strata and secondly, taking a thoroughly intermixed sample from the cuttings. When a person who is not a skilled agronomist is standing by a field it may not be immediately apparent to him whether the fertilizer bands in the field are running East-West or North-South. However, if the slit trench is cut at an angle to the boundary of the field the trench will inevitably cross the fertilizer bands regardless of their orientation. The basic method can therefore, be stated alternatively in terms of the steps of, firstly, cutting a slit trench along a path at an angle to the boundary of a field; and, secondly, taking a thoroughly intermixed sample from the cuttings.

The Applicant conducted experiments using various forms of apparatus. The method can be performed using a travelling auger, a travelling chisel, a dragline, and the like. By far the most satisfactory results were obtained using a chain saw. In order to use a chain saw, such as chain saw 12, continuous chain 16 had to be modified by the addition of a number of tooth-like projections 38 which dig into the soil. It is preferable that tooth-like projections 38 be equally spaced to keep blade 14 balanced and ensure a smooth movement of continuous chain 16. The steps for the method using the chain saw are as follows. Firstly, engaging a blade of a chain saw having a plurality of equally spaced tooth-like projections in the soil. Secondly, dragging the chain saw backwards in direction 46 to cut a slit trench to a depth D below surface 48 of approximately 6 inches and a width W of approximately $\frac{1}{2}$ of an inch along a path transverse to bands of fertilizer in the soil. Thirdly, taking a thoroughly intermixed sample from the cuttings.

The depth of 6 inches is recommended by the applicant in order to ensure that samples are taken from all bands of fertilizer within the soil. A depth of less than 6 inches may miss a fertilizer band. A depth in excess of 6 inches is not likely to provide any improvement in the accuracy of the results obtained. It has become practise in the profession that most fertilizer recommendations are calibrated against results of analyzing soil samples taken to a 6 inch depth. It is generally desirable to keep the width of the trench to a minimum. A wider trench can potentially produce such a soil volume that the efficacy of the method is lost. The purpose of the method is to take a "sample" of cuttings not to undertake an excavation. It can be difficult to obtain a representative intermixed sample by picking up the cuttings adjacent to the trench. Soil sampling apparatus 10 developed by the applicant provides a number of advantages when used as an attachment to a chain saw.

The use and operation of soil sampling attachment 10 will now be described with reference to FIGS. 1 through 4. Container 18 is secured to blade 14 of chain saw 12 by bolts 36 which pass through holes 34 in bracket 32 and aligned holes (not shown) in blade 14. When correctly installed blade 14 of chain saw 12 extends through slot 24. Upon activation of continuous chain 16 of chain saw 12 soil cuttings are lifted out of the soil by tooth-like projections 38 and drop from blade 14 through mouth 22 to accumulate in container 18. Mud guard 26 serves to confine the spray of cuttings thrown by tooth-like projections 38 on continuous chain 16. Soil sampling attachment 10 is placed on a groundsurface (not shown) with contact surface 30 of guide 28 engaging the groundsurface. The positioning of contact surface 30 in relation to blade 14 ensures that blade 14 is maintained at a preselected depth. The angle of contact surface 30 in relation to blade 14 ensures that the angle of penetration of blade 14 is always the same. Chain saw 12 is then pulled slowly backwards across the fertilizer bands to form a slit trench.

To ensure the accuracy of the results the Applicant recommends that 6 samples be taken. It will be noted that this is a considerably fewer number of samples than is required with other known methods. Each of the slit trenches should be cut for a sufficient length to transverse two bands, when the spacing of the bands is known. When the spacing of the bands is not known, the Applicant recommends that the length of the slit trench vary with the nature of the crop. Crops such as cereal grains generally have narrow fertilizer band spacing and a slit trench of 16 inches would be sufficient. Crops such as corn generally have wider band spacing and a slit trench of 32 inches would be more appropriate. The Applicant has found that the cutting action of the chain saw serves to intermix the sample, whereas with the coring methods previously used the samples were gathered in a pail and mixed by hand. The applicant has found that the chain saw is self cleaning, whereas with the coring methods previously used considerable effort was required to dislodge samples from the tubular coring device used, this was particularly true in soils rich in clay.

In order to emphasize to one skilled in the art the significance of the difference in the results obtained with the present method as compared to known coring methods, the Applicant can provide by way of example the results of a test plot. Core samples taken from a field banded with phosphate fertilizer at seven inch spacing between bands ranged from a low of 16 to a high of 160 parts per million of phosphorus. The actual results from the 12 coring samples taken were 20, 16, 19, 19, 100, 91, 107, 24, 24, 160, 25, and 20. Samples taken from the same field with a chain saw having the preferred attachment ranged between a low of 30 to a high of 40 parts per million of phosphorous. The actual results of the 5 samples taken were 40, 34, 30, 36, and 36.

It will be apparent to one skilled in the art that the preferred method can be practised using apparatus other than soil sampling attachment 10. It will further be apparent to one skilled in the art that modifications can be made to soil sampling attachment 10 without departing from the substance of the invention.

The embodiments of the invention in which an exclusive property or privilege is claimed are defined as follows:

1. A method of taking soil samples, comprising the steps of:
   a. cutting at least one slit trench along a path transverse to bands of fertilizer in the soil; and
   b. taking a thoroughly intermixed sample from the cuttings.

2. A method of taking soil samples as defined in claim 1, wherein the trench is cut using a blade of a chain saw, the blade of the chain saw having a plurality of equally spaced tooth-like projections.

3. A method of taking soil samples as defined in claim 2, including the step of engaging the blade of the chain saw in the soil and then dragging the chain saw backwards to form said at least one slit trench.

4. A method of taking soil samples as defined in claim 1, the trench being cut to a depth of approximately 6 inches.

5. A method of taking soil samples as defined in claim 1, the trench being cut with a width of approximately $\frac{1}{2}$ of an inch.

6. A method of taking soil samples, comprising the steps of:
   a. engaging a blade of a chain saw having a plurality of equally spaced tooth-like projections in the soil;
   b. dragging the chain saw backwards to cut a slit trench to a depth of approximately 6 inches and a width of approximately $\frac{1}{2}$ of an inch along a path transverse to bands of fertilizer in the soil; and
   c. taking a thoroughly intermixed sample from the cuttings.

* * * * *